United States Patent
Sevcik et al.

(10) Patent No.: US 6,607,385 B1
(45) Date of Patent: Aug. 19, 2003

(54) METHOD AND DEVICE FOR LIMITING THE TORQUE OF DENTAL AND SURGICAL HANDPIECES

(75) Inventors: Roland Sevcik, Bad Reichenhall (DE); Johann Fersterer, Lamprechtshausen (AT)

(73) Assignee: W & H Dentalwerk Bürmoos GmbH, Bürmoos (AT)

( * ) Notice: Subject to any disclaimer, the term of this patent is extended or adjusted under 35 U.S.C. 154(b) by 0 days.

(21) Appl. No.: 09/660,717

(22) Filed: Sep. 13, 2000

(30) Foreign Application Priority Data

Sep. 17, 1999 (AT) .............................................. 1595/99

(51) Int. Cl.[7] .............................. A61C 1/02; A61C 3/00
(52) U.S. Cl. ........................ 433/98; 433/114; 310/75 D
(58) Field of Search ........................... 433/98, 99, 114; 310/94, 75 D

(56) References Cited

U.S. PATENT DOCUMENTS

| | | | | |
|---|---|---|---|---|
| 5,357,179 A | * | 10/1994 | Abbagnaro et al. | ........... 318/17 |
| 5,476,014 A | * | 12/1995 | Lampe et al. | ............ 73/862.23 |
| 5,483,114 A | * | 1/1996 | Fenner | ..................... 310/75 D |
| 5,538,423 A | * | 7/1996 | Coss et al. | ..................... 433/27 |

* cited by examiner

Primary Examiner—John J. Wilson
(74) Attorney, Agent, or Firm—Friedrich Kueffner

(57) ABSTRACT

In a method for controlling a torque of a motor of dental and surgical handpieces to not exceed a set-point value when screwing in implant members, a motor current for applying the set-point torque is determined immediately before screwing in an implant member with the handpiece and the motor current is limited to the set point value with a motor control during subsequent screwing in of the implant member. The device for carrying out the method has a torque limiter, connectable to a tool receptacle of a handpiece, and a motor current measuring device for measuring a motor current of the motor of the handpiece.

5 Claims, 1 Drawing Sheet

METHOD AND DEVICE FOR LIMITING THE TORQUE OF DENTAL AND SURGICAL HANDPIECES

BACKGROUND OF THE INVENTION

1. Field of the Invention

The invention relates to a method and a device for limiting the torque of dental and surgical handpieces.

2. Description of the Related Art

Several surgical procedures, especially in regard to tooth implantation in the jaw area, are known in which the implant members which are provided with a thread are to be screwed into pre-drilled holes in the bone. (In this context, the term "implant member" is generally meant to include, for reasons of simplification, implants, implant carriers as well as closure screws or supra structure screws.) For this purpose, it is necessary to limit the torque of the electrically operated tool, with which the tightening or screwing action is carried out, to a preset limit value in order to reliably prevent a penetration depth that is too deep, damage of the bone mass, or stripping of the thread in the bone which is usually being cut by the thread of the implant member.

For example, immediately after positioning the implant, closure screws are screwed in and, when working in the jaw area, the gums are closed above the implant and allowed to heal. After approximately half a year or even longer, the closure screw is removed and an implant supra structure is connected to the implant by means of a supra structure screw. This supra structure screw must be screwed or tightened to such an extent that the supra structure screw (for example, an artificial tooth) is never seated loosely within the implant; however, on the other hand, the supra structure screw may never pull the implant out of the bone during tightening.

Based on practical experience and examinations of patients, the maximum torque to be applied is determined, and one is then presented with the problem of not exceeding this torque by the employed tool, for example, an angle piece.

In such a known method, the correlation between the torque and the motor current, provided by the manufacturer, is used in order to either limit the current or switch off the current to the motor and thereby terminate the screwing process when reaching the set point value, which is determined by continuously measuring the motor current. In this method, it has been shown to be disadvantageous that the aging process of the tool, by means of insufficient or excessive lubrication, by wear of the mechanical gear, or possibly by exchanging the mechanical drive, significant deviations of the actually applied torque from the preadjusted torque will result for the same motor current.

This has the consequence that the implant members are either tightened too tightly, which may cause all of the aforementioned problems and injuries, or too loosely, which may result in not only the implant carrier but also the implant mounted thereon becoming loose or even detaching, and a treatment of the patient must be repeated, if this is even possible.

Another occurring danger is the so-called too-loose screwing action of such implant parts, be it as a result of incorrectly calibrated handpieces or as a result of the incorrectly estimated torque requirement.

SUMMARY OF THE INVENTION

It is an object of the present invention to prevent these risks and disadvantages and to provide a method and a device with which the determined maximum torque can be reliably and safely observed. In a preferred variant it is also desired to monitor when a set point minimal torque is reached.

In accordance with the present invention, this is achieved in that, immediately before the screwing of the implant or implant carrier by means of a surgical handpiece, the motor current required for the application of the set point torque is determined and that, by means of the motor control, the motor current is limited to this value in the subsequent screwing action.

Since the measurement is carried out immediately before the screwing action, all tolerances and imprecisions can be compensated since the same conditions are indeed present during the measurement as well as the immediately following treatment. The term "immediately preceding" or "immediately following" is understood in the context of the invention such that between the measurement and the treatment no cleaning, lubricating, or servicing tasks and, in particular, no disassembly of the handpiece are carried out.

The device according to the invention comprises a device for applying a constant adjustable braking (tensioning) torque, preferably in the form of a hysteresis tension device, and a device for measuring the motor current so that the surgical handpiece is loaded during the calibration with the set-point torque and the correlation between the set point torque and the motor current is determined unequivocally.

Such hysteresis tension devices are known, for example, from the textile industry, the paper industry, the foil manufacturing industry, the measuring technology, and various other fields of application and are commercially available.

The function of such hysteresis tension devices is based on the magnetic force effect of poles attracting one another in synchronous running and on constant magnetic reversal of a permanent magnet material in the slip area. Manufacturers of such devices are, for example, MOBAC GmbH, Kiel, Germany, or ZF Friedrichshafen AG, Friedrichshafen, Germany.

DESCRIPTION OF THE PREFERRED EMBODIMENTS

Figure 1:
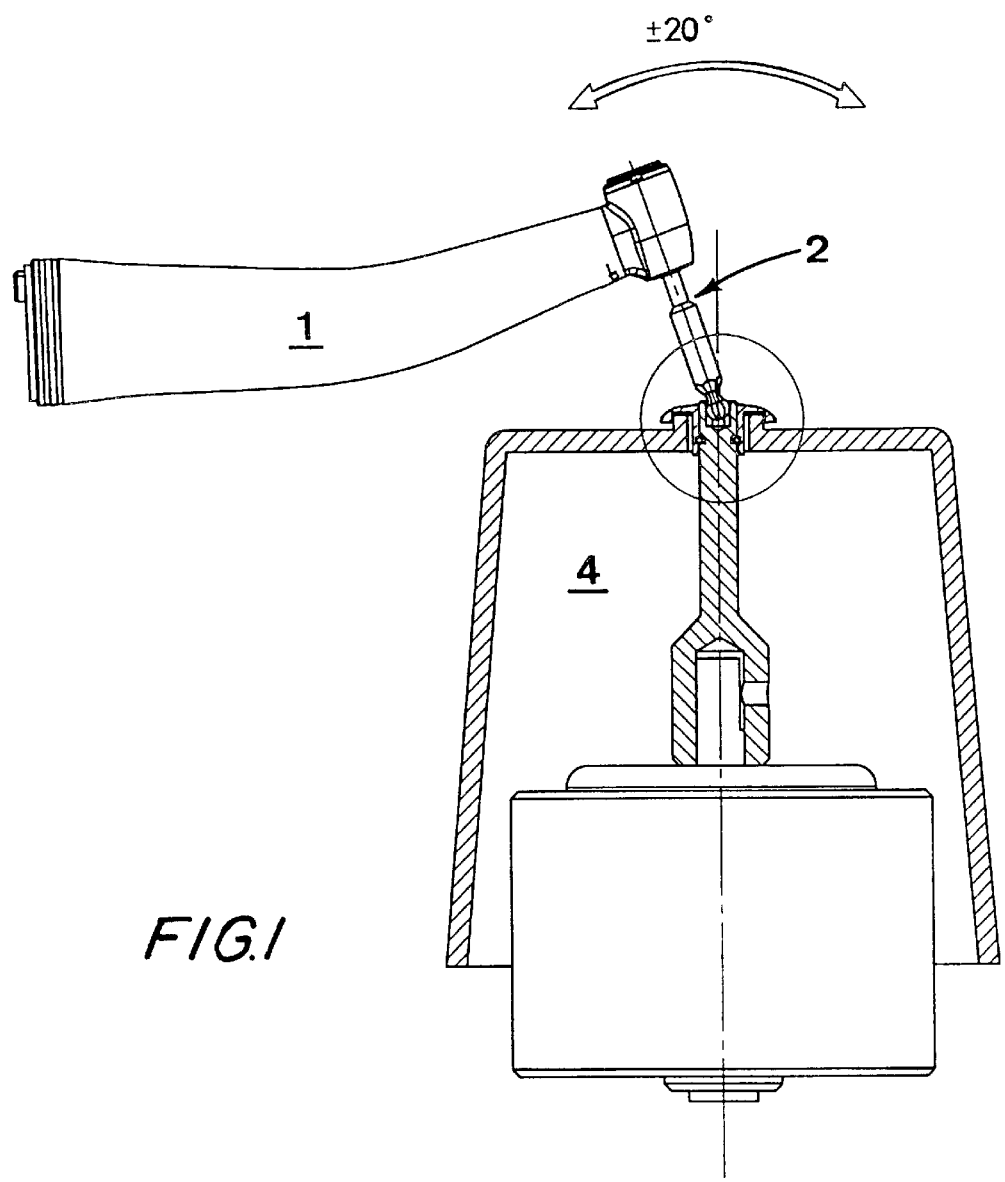
FIG. 1 is a schematic view of the measuring arrangement with hysteresis tension device according to the invention, partially in cross-section.

In order to carry out the calibration of the motor current according to the invention before the screwing action for an implant member, a surgical handpiece 1 is provided with a suitable connecting pin 2 which is clamped with one end into the tool receptacle of the handpiece 1. During the calibration process the connecting pin 2 engages with its lower end, preferably in a positive locking way, the receiving member 3 of a hysteresis tension device 4 (see FIG. 1).

The connecting pin 2 is made of sterilizable material and is to be sterilized before each use in order not to contaminate the tool receptacle of the handpiece 1. Furthermore, it is preferably dimensioned relatively large in order to prevent any contact between the sterilized handpiece 1 and the unsterilized receiving member 3 of the hysteresis tension device 4.

Figure 2:
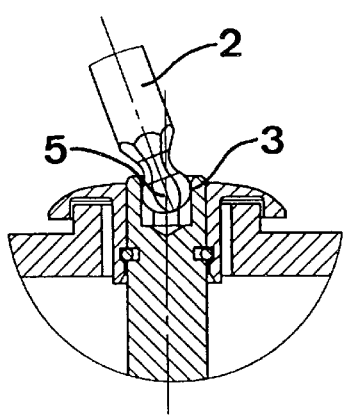
FIG. 2 shows a detail of the connecting pin and the receiving member of the hysteresis tension device.

The receiving member 3, as is illustrated in the detail drawing FIG. 2, is designed such that canting of the connecting pin 2 relative to the axis of rotation of the hysteresis tension device can be relatively easily compensated up to about 20°.

This is achieved by providing a substantially spherical-polygonal end 5 on the connecting pin 2 which engages a corresponding hollow polygonal recess of the receiving member 3 of the hysteresis tension device 4 and is surrounded by the recess.

The hysteresis tension device 4 is adjusted to a torque value which is preset by the surgeon, the motor of the handpiece 1 is started up, and the motor current is increased continuously until the pre-adjusted torque is reached. During this time period, the motor current is continuously measured by a motor current measuring device and in this way it is determined which motor current is present at the pre-adjusted torque.

The handpiece control is then adjusted, either manually or by a control device, which control device is then also preferably connected to.the hysteresis tension device and its circuitry and directly takes up its values, to this value which is the maximum value. The connecting pin 2 is subsequently removed from the tool receptacle of the handpiece 1, and the implant member to be screwed in is then connected thereto and then screwed into the bone.

FIG. 3 shows purely schematically a control arrangement of the device according to the invention. The hysteresis tension device 4 includes an electronic control device 7 for adjusting the desired torque. The handpiece 1 whose torque/motor current ratio is to be determined is inserted into the receptacle 3 (FIG. 2) of the device 4 and is rotated by means of its motor control 6 against the braking moment of the hysteresis tension device in the direction of rotation. When the desired torque has been reached, the motor current is measured by the current measuring device 8 and the obtained value is indicated and/or saved. In a preferred embodiment the motor control 6 is connected directly to the combined control device/measuring device 7/8 in order to be able to employ the measured values directly and thus free of errors.

In this connection, the control of the drive of the handpiece is performed such that the implant member rotates with a constant, pre-set speed so that during the course of the screwing process, during which frequently the thread in the bone is also to be cut, the torque which is required for maintaining a constant rotational speed increases continuously which causes the control of the handpiece motor to increase the motor current continuously.

This increase of the motor current is then monitored by a second control stage, and this second control stage, when the determined motor current of the motor, which has been measured immediately beforehand, has been reached, switches off the current supply to the motor and the drive is thus turned off. Accordingly, by releasing the tool or workpiece clamping device the implant member, which has now been screwed in, can be separated from the tool receptacle of the handpiece. With this procedure, it is ensured that the implant member has been threaded or screwed into the bone with the set point torque.

Since the control of the motor current is basically known in the prior art and since a person skilled in the art of control technology is easily capable of connecting the hysteresis tension device/strength of current measurement with the motor control, no further explanations in this a regard are provided in this context.

In a preferred embodiment of the invention, it is suggested that the actual motor current, i.e., the actual torque, is determined during the screwing process and at least its maximum value is stored. In this way, should it be necessary to interrupt the screwing operation before reaching the switch-off current value because it is apparent that the implant member has reached the predetermined threading depth, it is possible for the operator to determine the course of the torque or how great the maximum torque that has occurred at this point has been.

This knowledge allows at least an ex post facto estimate of the achieved securing force. When the entire course of the torque is known, it is also possible to estimate whether possibly a stripping of the thread cut into the jaw has occurred. For example, this would be the case when subsequent to a period with relatively high torque a torque drop is observed. With this knowledge it is possible to make decisions on further steps that are required with substantially greater reliability than before.

The invention is not limited to the described and illustrated embodiment but can also be varied in different ways. For example, for further improving the conformity of the course of operation during calibration and screwing, respectively, it is possible to drive the handpiece during the calibration step with the rotational speed of the screwing step and to control the hysteresis tension device continuously or stepwise up to the point of the set point torque and to measure the current while doing so.

In any case, with the measures according to the invention the errors of prior art devices, including the worst-case scenarios in which a wrong gear has been used in the angled handpiece, can be avoided without requiring a complicated (and thus again error-prone) or time-consuming procedure. The only steps required are the insertion of the connecting pin, the activation of the calibrating device, and, subsequent to the determination of the maximum value of the motor current, replacement of the connecting pin with the implant member, whereupon the latter can be screwed in.

While specific embodiments of the invention have been shown and described in detail to illustrate the inventive principles, it will be understood that the invention may be embodied otherwise without departing from such principles.

What is claimed is:

1. A method for controlling the torque of a motor of dental and surgical handpieces to not exceed a set-point value when screwing in implant members, the method comprising the steps of determining a motor current required for applying the set-point torque immediately before screwing in an implant member with the handpiece and of limiting the motor current to the set point value with a motor control during subsequent screwing of the implant member.

2. The method according to claim 1, wherein no disassembly, cleaning, lubricating or servicing of the handpieces is carried out between the step of determining the motor current and the subsequent screwing of the implant member.

3. The method according to claim 1, wherein during screwing an actual motor current is continuously or periodically measured and wherein at least a maximum motor current value is stored so as to be retrievable or displayable.

4. A device for controlling the torque of a motor of dental and surgical handpieces to not exceed a set-point value when screwing in implant members, the device comprising a torque limiter configured to be connected to a tool receptacle of a handpiece and to be adjusted to a set point torque, and comprising a motor current measuring device configured to measure a motor current of the motor of the handpiece at the set point torque, wherein the motor current measured at the set point torque is displayed or saved in a motor control of the handpiece for use in an immediately following screwing action of an implant member carried out by the handpiece.

5. The device according to claim 4, wherein the torque limiter is a hysteresis tension device.

* * * * *